United States Patent
Zhao et al.

(10) Patent No.: US 8,251,929 B2
(45) Date of Patent: Aug. 28, 2012

(54) INTEGRATED ULTRASOUND THERAPY TRANSDUCER ASSEMBLY

(75) Inventors: Chunliang Zhao, Chougqing (CN); Zhibiao Wang, Chongqing (CN); Zhilong Wang, Chongqing (CN); Jin Bai, Chongqing (CN)

(73) Assignee: Chongqing Haifu (Hifu) Technology Co., Ltd., Chongqing (CN)

( * ) Notice: Subject to any disclaimer, the term of this patent is extended or adjusted under 35 U.S.C. 154(b) by 885 days.

(21) Appl. No.: 11/794,929

(22) PCT Filed: Sep. 2, 2005

(86) PCT No.: PCT/CN2005/001390
§ 371 (c)(1),
(2), (4) Date: Nov. 26, 2007

(87) PCT Pub. No.: WO2006/072199
PCT Pub. Date: Jul. 13, 2006

(65) Prior Publication Data
US 2008/0287835 A1 Nov. 20, 2008

(30) Foreign Application Priority Data
Jan. 10, 2005 (CN) .......................... 2005 1 0000349

(51) Int. Cl.
*A61N 7/00* (2006.01)
(52) U.S. Cl. ................. 601/2; 601/3; 600/459; 600/439
(58) Field of Classification Search ................. 600/439, 600/459
See application file for complete search history.

(56) References Cited

U.S. PATENT DOCUMENTS

| | | | | |
|---|---|---|---|---|
| 5,601,526 A | * | 2/1997 | Chapelon et al. | 601/3 |
| 5,720,287 A | * | 2/1998 | Chapelon et al. | 600/439 |
| 6,126,619 A | * | 10/2000 | Peterson et al. | 601/2 |
| 6,666,835 B2 | | 12/2003 | Martin et al. | |
| 2006/0058707 A1 | * | 3/2006 | Barthe et al. | 601/2 |

FOREIGN PATENT DOCUMENTS

| | | |
|---|---|---|
| CN | 2657706 | 11/2004 |
| EP | 0774276 A2 | 5/1997 |
| EP | 0938913 | 1/1999 |
| GB | 2029159 A | 3/1980 |
| JP | 64037947 | 2/1989 |
| JP | 04044797 | 2/1992 |
| JP | 09155290 | 6/1997 |
| WO | 95/24159 | 9/1995 |
| WO | 0215768 A2 | 2/2002 |

\* cited by examiner

*Primary Examiner* — Long V. Le
*Assistant Examiner* — Farshad Negarestan
(74) *Attorney, Agent, or Firm* — The Webb Law Firm

(57) ABSTRACT

The present invention is to provide an integrated ultrasound therapy transducer. It includes a piezoelectric transducer to generate therapy ultrasound, a support to support the piezoelectric transducer, a power amplifying module to drive the piezoelectric transducer. Wherein both the power amplifying module and the piezoelectric transducer are installed within the enclosure of the therapy transducer. The advantages of the integrated ultrasound therapy transducer assembly of the present invention include minimizing ultrasound therapy equipment and to decrease its volume and weight; reducing the electromagnetic interference and radiation greatly; and realizing the consistent performances of the ultrasound therapy equipments in mass productions and making the ultrasound therapy equipments have interchangeability.

7 Claims, 3 Drawing Sheets

INTEGRATED ULTRASOUND THERAPY TRANSDUCER ASSEMBLY

FIELD OF THE INVENTION

This invention relates to a component of ultrasound therapy equipment. In particular this invention relates to a transducer assembly of ultrasound therapy equipment.

BACKGROUND OF THE INVENTION

In the clinical applications of ultrasound therapy equipment, it is urgent to require minimizing the volume and weight of the equipment, including the overall weight and volume of the equipment and the weight and volume of each component of the equipment, such as transducer assembly. The existing ultrasound therapy transducers are shown in FIG. 1 and FIG. 2. As shown in these figures, the power amplifying module 1 of the existing ultrasound therapy equipment is installed separately from the therapy transducer 5 and the power amplifying module is connected to the therapy transducer 5 through cable 3. This structure with a big size is heavy and it makes the signal transmission and resistance matching difficult. Installing the power amplifying module 1 and the therapy transducer 5 separately makes the high-frequency and high-power electric signals to be transmitted to the therapy transducer 5 by cable 3. If the parameters of the cable 3 are selected inappropriately or the cable 3 is too long, the bad electromagnetic pollution would be brought.

Installing the therapy transducer and the power amplifying module separately makes the ultrasound therapy equipment have a big size and each component be installed separately. Such designs bring a lot of problems on engineering designs. Because the resistance and acoustic emission efficiency of each therapy transducer are different, installing separately makes the consistency and interchangeability of both the therapy transducer and the power amplifying module more difficult to be solved.

SUMMARY OF THE INVENTION

An object of the present invention is to solve the above-mentioned problems on installing the therapy transducer separately from the power amplifying module and to provide an integrated ultrasound therapy transducer assembly accordingly to overcome the shortcomings of separate installation of the therapy transducer from the power amplifying module, to improve the resistance matching between the therapy transducer and the power amplifying module, and the consistency and interchangeability of electromagnetic compatibility, and to minimize the therapy equipment.

The present invention provides an integrated ultrasound therapy transducer assembly. It includes a piezoelectric transducer to generate therapy ultrasound, a support to support the piezoelectric transducer, a power amplifying module to drive the piezoelectric transducer. Wherein both the power amplifying module and the piezoelectric transducer are installed within the enclosure of the therapy transducer.

The power amplifying module may be installed at the back side of piezoelectric transducer and it is located at opposite side of acoustic emitting surface of piezoelectric transducer. The radiating surface of the power amplifying module is coupled closely to the enclosure of the therapy transducer assembly and accordingly the enclosure of the integrated therapy transducer assembly is used as the radiating board of the power amplifying module.

A passage, in which the cooling fluid may flow, is formed between the radiating surface of the power amplifying module and the piezoelectric transducer, so that the circulating cooling fluid, which is flowed into the enclosure of the therapy transducer can be used to cool the power amplifying module.

The cross section of the power amplifying module of the integrated ultrasound therapy transducer assembly may be circular and is adaptive to the shape of the therapy transducer enclosure.

The power amplifying module of the integrated ultrasound therapy transducer assembly includes the resistance transforming components, such as high-frequency transformer, capacitor and inductor.

The cables of the integrated ultrasound therapy transducer assembly include two power cords, one coaxial cable and two or more other control cables.

The piezoelectric transducer may adopt flat piezoelectric crystals or self-focusing piezoelectric crystals. The acoustic beams emitting from piezoelectric transducer may be focused by acoustic lends. The piezoelectric transducer may be the phased array transducer or multi-elements array transducer.

The advantages of the integrated ultrasound therapy transducer assembly of the present invention are:

1. minimizing ultrasound therapy equipment and to decrease its volume and weight;
2. reducing the electromagnetic interference and radiation greatly; and
3. realizing the consistent performances of the ultrasound therapy equipments in mass productions and making the ultrasound therapy equipments have interchangeability.

The numbers in these figures are explained as below:

| 1 Power amplifying module | 2 Control module | 3 Cable |
|---|---|---|
| 4 Piezoelectric transducer | 5 Therapy transducer enclosure | |
| 6 Acoustic lens | 7 Power amplifying module input interface | |
| 8 Separating board | 9 Cooling fluid inlet | |
| 10 Cooling fluid outlet | | |
| 12 Power amplifying module output cable | 13 Radiator | |

DESCRIPTION OF THE PREFERRED EMBODIMENT

Figure 1:
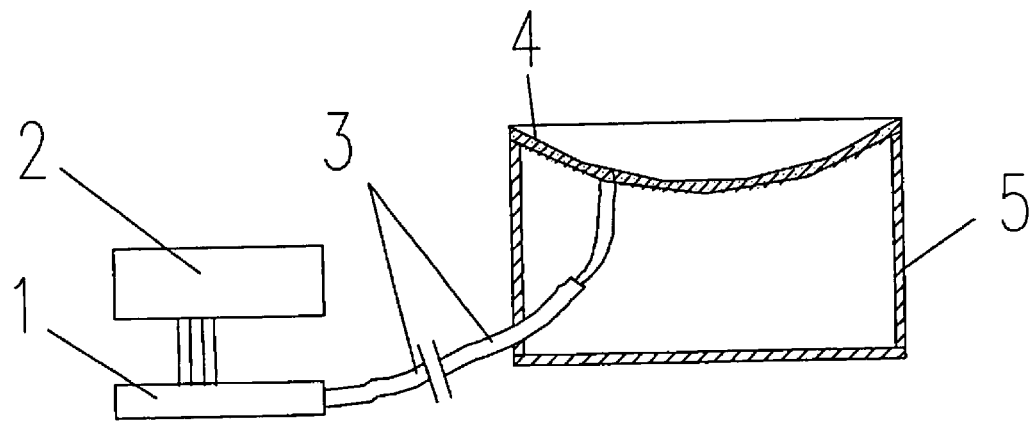
FIG. 1 is a schematic diagram of sections of existing ultrasound therapy transducers to illustrate the installation relationships between the transducer and the power amplifying module.
Figure 2:
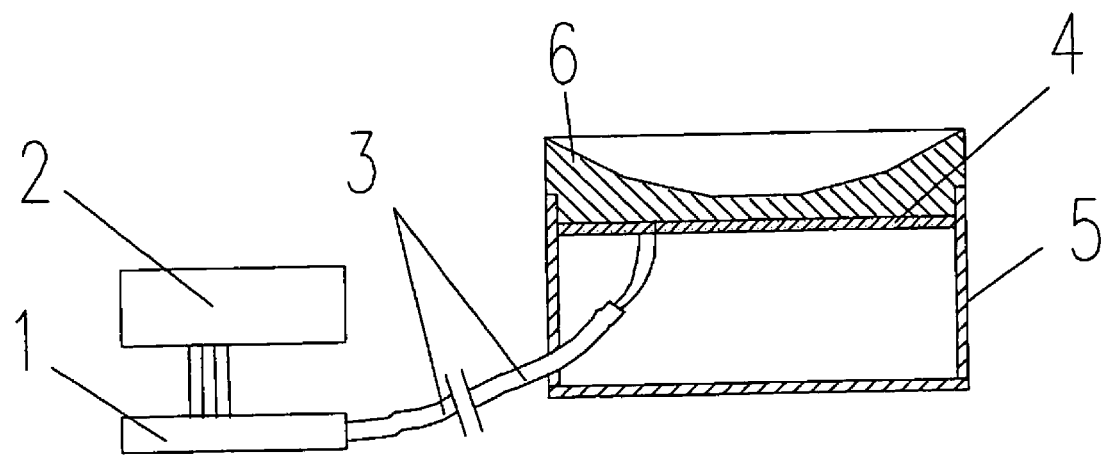
FIG. 2 is a schematic diagram of sections of existing ultrasound therapy transducer to illustrate the installation relationships between the transducer and the power amplifying module.
Figure 3:
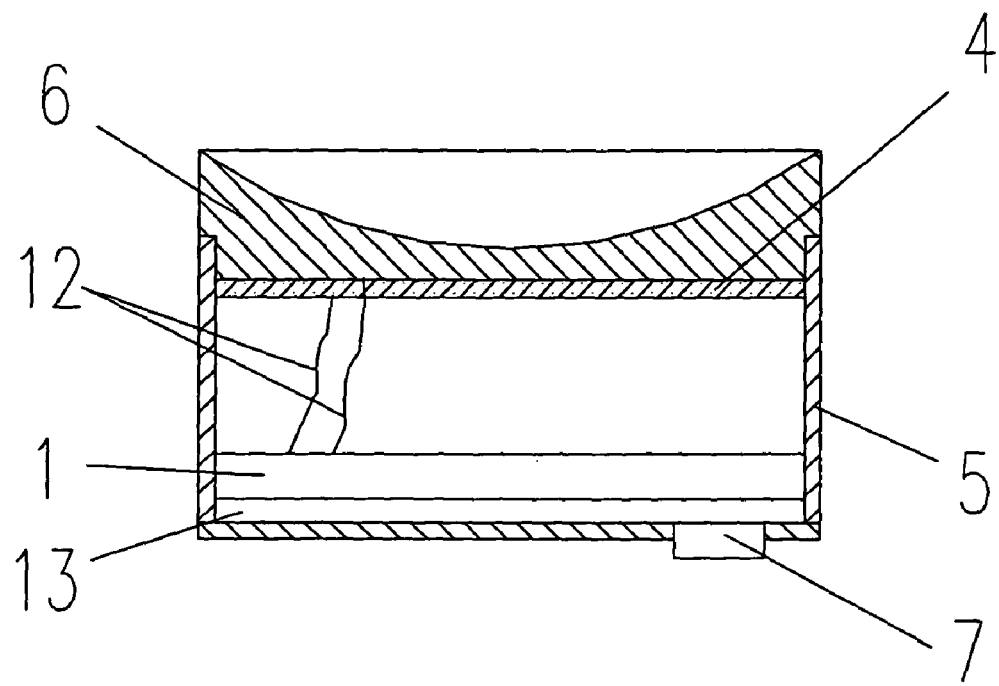
FIG. 3 is a schematic diagram to illustrate the installation relationships between the ultrasound therapy transducer and the power amplifying module.

The preferred embodiments of the present invention are explained as below:

FIG. 3 illustrates one embodiment of the present invention. The assembly here includes power amplifying module 1, piezoelectric transducer 4, enclosure 5, acoustic lens 6, power amplifying module input interface 7, power amplifying module output cable 12 and radiator 13. The piezoelectric transducer 4 generating therapeutic ultrasound waves and the acoustic lens 6 are adhered together using glue. The acoustic lens 6 is installed on the therapy transducer enclosure 5. The power amplifying module 1 is installed at the back side of the piezoelectric transducer 4 and it is located at opposite side of acoustic emitting surface of the piezoelectric transducer 4. The radiating surface of the power amplifying module 1 is coupled closely to the therapy transducer enclosure 5 and accordingly the therapy transducer enclosure 5 is used as the radiating board of the power amplifying module 1. Here, the heat generated by the power amplifying module 1 is radiated by radiator 13 and the therapy transducer enclosure 5.

The power amplifying module output cable 12 is connected to two electrodes of the piezoelectric transducer 4.

The power amplifying module input interface 7 is used to input the external control signals and the driving power. It is located at the bottom or at the side of the integrated ultrasound therapy transducer assembly.

The cross section of the power amplifying module 1 is circular in order to fit the shape of the therapy transducer enclosure 5.

Figure 4:
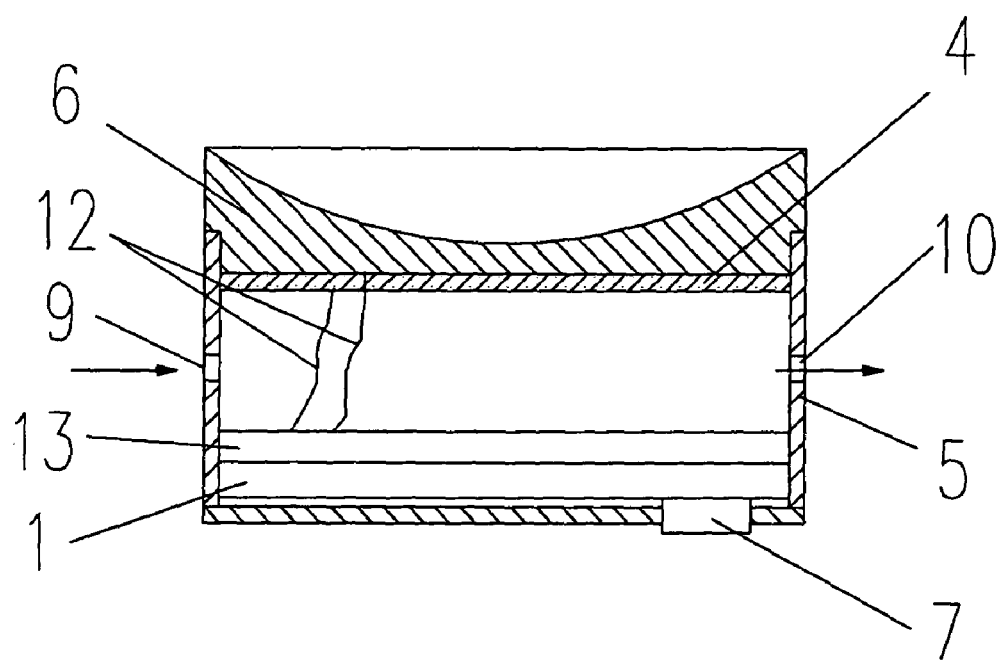
FIG. 4 is a schematic diagram to illustrate the installation relationships between the ultrasound therapy transducer and the power amplifying module.

FIG. 4 illustrates the second embodiment of the present invention. The assembly here includes power amplifying module 1, piezoelectric transducer 4, therapy transducer enclosure 5, acoustic lens 6, power amplifying module input interface 7, cooling fluid inlet 9, cooling fluid outlet 10, power amplifying module output cable 12 and radiator 13. The piezoelectric transducer 4 generating therapeutic ultrasound waves and the acoustic lens 6 are adhered together using glue. The acoustic lens 6 is installed on the therapy transducer enclosure 5. The power amplifying module 1 is installed at the back side of the piezoelectric transducer 4 and it is located at opposite side of acoustic emitting surface of the piezoelectric transducer 4. A passage, in which the cooling fluid may flow, is formed between the radiating surface of the power amplifying module 1 and the piezoelectric transducer 4. As the arrow direction shown in FIG. 4, the cooling fluid flows from the inlet 9 into the integrated ultrasound therapy transducer so as to cool the power amplifying module 1 and then flows out through the outlet 10. Said cooling fluid may be the circulating gas or liquid.

The power amplifying module output cable 12 is connected to two electrodes of the piezoelectric transducer 4.

The power amplifying module input interface 7 is used to input the external control signals and the driving power. It is located at the bottom or at the side of the integrated ultrasound therapy transducer assembly.

The power amplifying module 1 is in a circular-shape in order to fit the shape of the therapy transducer enclosure 5 so that the areas of the space can be utilized effectively.

Figure 5:
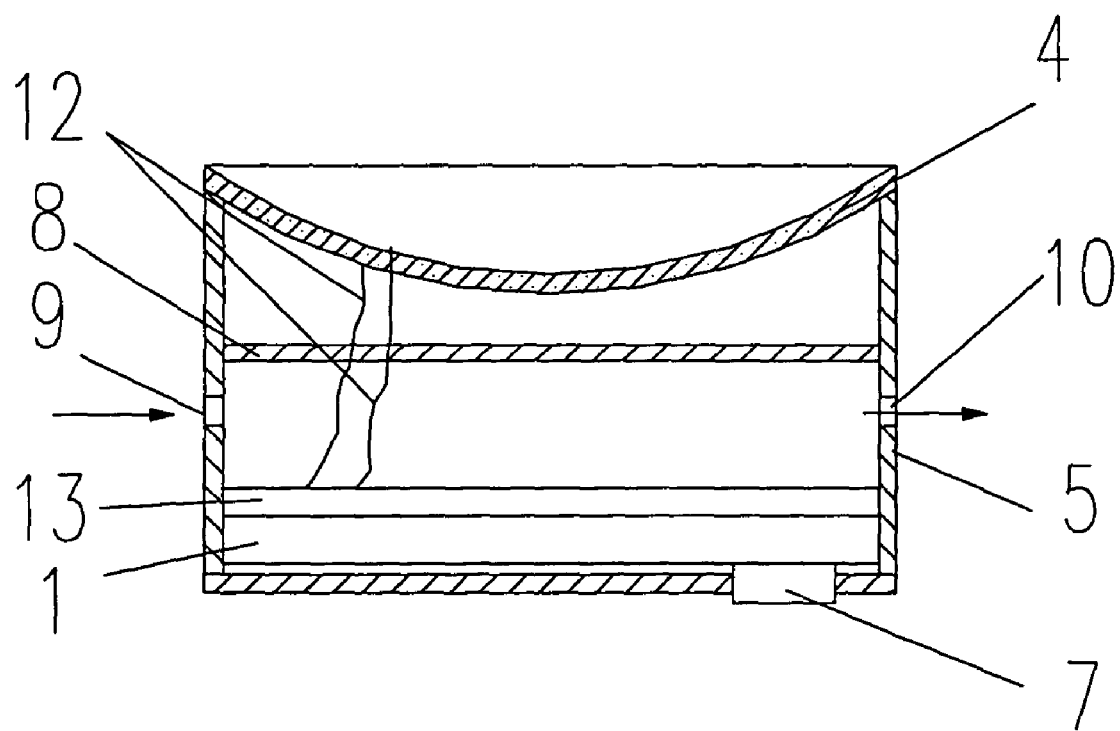
FIG. 5 is a schematic diagram to illustrate the installation relationships between the ultrasound therapy transducer and the power amplifying module.

FIG. 5 illustrates the third embodiment of the present invention. The assembly here includes power amplifying module 1, piezoelectric transducer 4, therapy transducer enclosure 5, power amplifying module input interface 7, separating board 8, cooling fluid inlet 9, cooling fluid outlet 10, power amplifying module output cable 12 and radiator 13. There is a separating board 8 inside the piezoelectric transducer 4 and the power amplifying module 1. It separates the integrated ultrasound therapy transducer assembly into two parts. As the arrow direction shown in FIG. 5, the cooling fluid flows from the inlet 9 into the lower part of the integrated ultrasound therapy transducer so as to cool the power amplifying module 1 and then flows out through the outlet 10. Said cooling fluid may be the circulating gas or liquid. Other structures in FIG. 5 are the same in FIG. 4 and they are not repeated here.

The invention claimed is:

1. An integrated ultrasound therapy transducer assembly comprising:

an enclosure;

a piezoelectric transducer to generate therapy ultrasound;

a support to support the piezoelectric transducer; and a power amplifying module to drive the piezoelectric transducer, wherein the power amplifying module and the piezoelectric transducer are installed within the enclosure, and wherein a passage for circulating a cooling fluid is formed between a portion of a radiating surface of the power amplifying module and the piezoelectric transducer such that the cooling fluid flowing in the passage simultaneously cools the piezoelectric transducer and the power amplifying module, wherein said power amplifying module is installed at a back side of the piezoelectric transducer and located at an opposite side of an acoustic emitting surface of the piezoelectric transducer, wherein the power amplifying module is directly connected to a back wall and side walls of the enclosure, and wherein the enclosure is used as a radiating board of the power amplifying module.

2. The integrated ultrasound therapy transducer assembly according to claim 1, wherein a cross section of said power amplifying module is circular and is adapted to a shape of the enclosure.

3. The integrated ultrasound therapy transducer assembly according to claim 1, wherein said piezoelectric transducer is a flat piezoelectric crystal.

4. The integrated ultrasound therapy transducer assembly according to claim 3, wherein ultrasound waves emitting from said piezoelectric transducer are focused by an acoustic lens.

5. The integrated ultrasound therapy transducer assembly according to claim 1, wherein said piezoelectric transducer is a self-focusing piezoelectric crystal.

6. The integrated ultrasound therapy transducer assembly according to claim 1, wherein said piezoelectric transducer is a phased array ultrasound therapy transducer.

7. The integrated ultrasound therapy transducer assembly according to claim 1, wherein said piezoelectric transducer is a multi-elements array ultrasound therapy transducer.

* * * * *